United States Patent
Esser et al.

(10) Patent No.: US 10,343,966 B2
(45) Date of Patent: Jul. 9, 2019

(54) PROCESS FOR THE PRODUCTION OF 17-OXABICYCLO[14.1.0]HEPTADEC-8-ENE

(71) Applicant: SYMRISE AG, Holzminden (DE)

(72) Inventors: Peter Esser, Bevern (DE); Angela Köckritz, Berlin (DE); Andreas Martin, Berlin (DE); Diego Jaime, Rostock (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 15/790,464

(22) Filed: Oct. 23, 2017

(65) Prior Publication Data

US 2018/0179137 A1 Jun. 28, 2018

(30) Foreign Application Priority Data

Sep. 2, 2016 (EP) .................................... 16186941

(51) Int. Cl.
| | | |
|---|---|---|
| *C07C 45/27* | (2006.01) | |
| *B01J 31/04* | (2006.01) | |
| *C07D 301/12* | (2006.01) | |
| *C07F 11/00* | (2006.01) | |
| *B01J 31/02* | (2006.01) | |
| *B01J 37/04* | (2006.01) | |

(52) U.S. Cl.
CPC ........... *C07C 45/27* (2013.01); *B01J 31/0278* (2013.01); *B01J 31/0298* (2013.01); *B01J 37/04* (2013.01); *C07D 301/12* (2013.01); *C07F 11/005* (2013.01); *C07C 2602/32* (2017.05)

(58) Field of Classification Search
CPC .. C07C 45/27; C07C 2602/32; B01J 31/0278; B01J 31/0298; B01J 31/04; C07D 301/12
See application file for complete search history.

(56) References Cited

U.S. PATENT DOCUMENTS 7,846,886 B2 * 12/2010 Oertling ............... C07D 303/06
510/104

FOREIGN PATENT DOCUMENTS

| DE | 2111753 A1 | 3/1971 |
|---|---|---|
| EP | 0109273 A1 | 5/1984 |
| EP | 0434546 A1 | 6/1991 |
| WO | 2007090704 A1 | 8/2007 |

OTHER PUBLICATIONS

E. Kaczmarczyk et al., "Epoxidation of 1,4-diallyloxybutane to 1-allyloxy-4-glycidyloxybutane by the method of phase Transder catalysis," Journal of Molecular Catalysis A: Chemical, vol. 244, 2006, 6 pages.

P. Witte et al., "Self-Assembled Na12[WZn3(ZnW9O34)2] as an Industrially Attractive Multi-Purpose Catalyst for Oxidations with Aqueous Hydrogen Peroxide," Org. Proc. Res. Dev., Mar. 23, 2004, 8 pages.

B.D. Mookherjee et al., "Synthesis of racemic muscone and cyclopentadecanone (exaltone) from 1, 9-cyclohexadecadiene," The Journal of Organic Chemistry, American Chemical Society, US, Bd. 36, Nr. 22, Jan. 1, 1971, 6 pages.

* cited by examiner

*Primary Examiner* — Timothy R Rozof
(74) *Attorney, Agent, or Firm* — Hoffman Warnick LLC

(57) ABSTRACT

The invention relates to a process for producing 17-oxabi-cyclo[14.1.0]heptadec-8-ene comprising a reaction with the reactants cyclohexadeca-1,9-diene and hydrogen peroxide.

12 Claims, No Drawings

PROCESS FOR THE PRODUCTION OF 17-OXABICYCLO[14.1.0]HEPTADEC-8-ENE

FIELD OF THE INVENTION

The present invention relates to a process for producing 17-oxabicyclo[14.1.0]heptadec-8-ene from cyclohexadeca-1,9-diene (CHDD).

PRIOR ART

17-Oxabicyclo[14.1.0]heptadec-8-ene is an intermediate stage of the musk fragrance 8-cyclohexadecen-1-one and may be produced by already-known production processes. DE2111753 and DE112007000301 each disclose the production of 17-oxabicyclo[14.1.0]heptadec-8-ene from cyclohexadeca-1,9-diene using peroxy acids.

OBJECT OF THE INVENTION

It is the object of the present invention to selectively epoxidize cyclohexadeca-1,9-diene at a double bond to 17-oxabicyclo[14.1.0]heptadec-8-ene. The reaction must be capable of being carried out economically, with high yield, under sustainable conditions with high selectivity, minimal use of energy, minimal consumption of raw materials, few by-products, high reaction velocity, minimal system corrosion, and in an atom-efficient and environmentally friendly manner. In particular, the formation of undesired diepoxides is to be avoided or minimized because, among other things, these can be difficult to separate from the desired monoepoxides, and the expense of such separation is significant.

DESCRIPTION OF THE INVENTION

The process for producing 17-oxabicyclo[14.1.0]heptadec-8-ene comprises a reaction in which cyclohexadeca-1,9-diene and hydrogen peroxide are used as reactants.

The molecular relationship of cyclohexadeca-1,9-diene to hydrogen peroxide is, preferably, 1 less than 1, more preferably, 1:0.1-0.9, and, particularly preferably, 1:0.4-0.6.

Cyclohexadeca-1,9-diene and its production are already known, and it is also available commercially. It is often present as a mixture of stereoisomers.

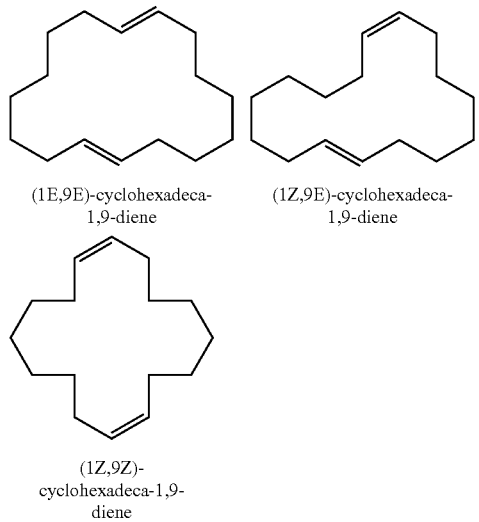

(1E,9E)-cyclohexadeca-1,9-diene   (1Z,9E)-cyclohexadeca-1,9-diene (1Z,9Z)-cyclohexadeca-1,9-diene Hydrogen peroxide ($H_2O_2$) and its production are likewise already known, and it is also available commercially.

A further advantage of the process is that there exists no compelling need to use halogen-containing solvents in the reaction, so that the reaction can be carried out without halogenated solvents—in particular, solvents containing chlorine. In this respect, the need to dispose of the halogenated solvent is eliminated, and there is no danger that undesired halogenated organic compounds will form. Halogen-free solvents such as aliphatic or cyclic hydrocarbons and alkylated aromatics are preferred.

The reaction of cyclohexadeca-1,9-diene and hydrogen peroxide can be carried out in a two-phase system. For example, this can be accomplished by adding to the reactants either no solvent or only very nonpolar solvents (such as toluene) or very polar solvents (such as water).

It is advantageous to use a catalyst in the process, wherein phosphorus-containing or/and tungsten-containing catalysts are especially suitable. Furthermore, the use of a phase transfer catalyst is also advantageous.

The catalyst and its active species are preferably allowed to develop in situ as catalyst precursors. One of the advantages of in situ formation consists in the fact that, unlike ex situ formation, the active species need not be isolated in order to be able to be used in the process. Phosphorus-containing catalyst precursors include, e.g., phosphoric acid, phosphonic acids such as hydroxymethylphosphonic acid and aminomethylphosphonic acid, phosphinic acids such as diphenylphosphinic acid or di(hydroxymethyl)phosphinic acid, and heteropoly acids such as tungstophosphoric acid or molybdophosphoric acid and their derivatives (e.g., lacunar heteropoly acids and polyoxometalates). A variation in the precursor of the phosphorus component is also possible. Therefore, in addition to $H_3PO_4$, phosphonic acids are very well suited. Hydroxymethylphosphonic acid and phenylphosphonic acid are particularly preferred in this instance.

Tungsten-containing catalyst precursors include, for example, water-soluble tungsten compounds, tungstates, tungsten(VI)-compounds, alkali tungstates, alkaline-earth metal tungstate, ammonium tungstate, or tungsten trioxide monohydrate. $Na_2WO_4$ is a specific example of a tungsten-containing catalyst precursor.

Examples of a phase transfer catalyst include tetraalkylammonium salt(s) or, preferably, one or more compounds of the formula,

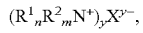

$(R^1{}_n R^2{}_m N^+)_y X^{y-}$, characterized in that $R^1$ and $R^2$ each mean C1-C30 n-alkyl, and $R^1$ is the same as or different from $R^2$, and the sum of m and n is 4, $X^{y-}$ equals $Cl^-$, $Br^-$, $I^-$, $HSO_4^-$, $SO_4^{2-}$, $H_2PO_4^-$, $HPO_4^{2-}$, $PO_4^{3-}$, $CH_3SO_3^-$, $CF_3SO_3^-$, $CH_3C_6H_4SO_3^-$, $ClO_3^-$, $ClO_4^-$, or $NO_3^-$, and the sum of m and n equals 4, and y equals 1, 2, or 3.

Preferred anions of the phase transfer catalyst include hydrogen sulfate anions, sulfonic acid anions, or dihydrogen phosphate anions, with hydrogen sulfate anions being particularly preferred.

One example of a phase transfer catalyst is Aliquat 336 ® (trioctylmethylammonium chloride).

It is advantageous if 1 to 3 methyl groups are located on the ammoniacal nitrogen, wherein the remaining alkyl groups on the ammoniacal nitrogen should then have a greater chain length of between 6 and 30 carbon atoms in the chain, with a preferred chain length being between 8 and 22 carbon atoms.

When mixing the tungsten and phosphate-containing catalyst precursors in the presence of hydrogen peroxide and water, peroxotungstophosphates are generated. It is assumed that many suitable peroxotungstophosphates have the $\{PO_4[WO(O_2)_2]_4\}^{3-}$ anion available.

The cationic component of the active species of the catalyst can be formed from the cation of a phase transfer catalyst; in particular, the cation of the phase transfer catalyst can have the formula, $$R^1{}_nR^2{}_mN^+,$$

characterized in that $R^1$ and $R^2$ each mean C1-C30 n-alkyl, and $R^1$ is the same as or different from $R^2$, and the sum of m and n is 4.

To produce the active species of the catalyst, an aqueous mixture/solution comprising at least one phosphorus-containing acid, at least one tungsten (VI) compound, and at least one phase transfer catalyst and, as the case may be, hydrogen peroxide, can be used. Table A contains examples of the tungsten-containing and phosphorus-containing catalyst precursors and phase transfer catalysts of such aqueous solutions.

TABLE A

| Ex. No. | Tungsten-containing catalyst precursor | Phosphorus-containing catalyst precursor | Phase transfer catalyst |
|---|---|---|---|
| 1 | $Na_2WO_4$ | $HOCH_2P(O)(OH)_2$ | $[CH_3(C_8H_{17})_3N]Cl$ |
| 2 | $Na_2WO_4$ | $HOCH_2P(O)(OH)_2$ | $[CH_3(C_8H_{17})_3N]HSO_4$ |
| 3* | $Na_2WO_4$ | $HOCH_2P(O)(OH)_2$ | $[CH_3(C_{18}H_{37})_3N]HSO_4$ |
| 4 | $Na_2WO_4$ | $C_6H_5P(O)(OH)_2$ | $[CH_3(C_8H_{17})_3N]Cl$ |
| 5 | $Na_2WO_4$ | $C_6H_5P(O)(OH)_2$ | $[CH_3(C_8H_{17})_3N]HSO_4$ |
| 6* | $Na_2WO_4$ | $C_6H_5P(O)(OH)_2$ | $[CH_3(C_{18}H_{37})_3N]Cl$ |
| 7 | $Na_2WO_4$ | $H_2NCH_2P(O)(OH)_2$ | $[CH_3(C_8H_{17})_3N]Cl$ |
| 8 | $Na_2WO_4$ | $H_2NCH_2P(O)(OH)_2$ | $[CH_3(C_8H_{17})_3N]HSO_4$ |
| 9 | $Na_2WO_4$ | $H_3PO_4$ | $[(C_4H_9)_4N]HSO_4$ |
| 10 | $Na_2WO_4$ | $H_3PO_4$ | $[CH_3(C_8H_{17})_3N]Cl$ |
| 11 | $Na_2WO_4$ | $H_3PO_4$ | $[CH_3(C_8H_{17})_3N]HSO_4$ |
| 12* | $Na_2WO_4$ | $H_3PO_4$ | $[(CH_3)_2(C_{18}H_{37})_2N]HSO_4$ |
| 13* | $Na_2WO_4$ | $H_3PO_4$ | $[(C_{18}H_{37})_4N]HSO_4$ |
| 14 | $Na_2WO_4$ | $H_3PO_4$ | $[(CH_3)_3(C_{16}H_{33})N]O_3SC_6H_4\text{-}4\text{-}CH_3$ |
| 15* | $Na_2WO_4$ | $H_3PO_4$ | $[CH_3(C_8H_{17})_3N]H_2PO_4$ |
| 16 | $Na_2WO_4$ | $(C_6H_5)_2P(O)OH$ | $[CH_3(C_8H_{17})_3N]HSO_4$ |
| 17 | $Na_2WO_4$ | $H_2NCH_2P(O)(OH)_2$ | $[CH_3(C_8H_{17})_3N]HSO_4$ |
| 18 | $Na_2WO_4$ | $H_3PO_4$ | $[CH_3(C_8H_{17})_3N]HSO_4$ |
| 19 | $Na_2WO_4$ | $HOCH_2P(O)(OH)_2$ | $[CH_3(C_8H_{17})_3N]HSO_4$ |
| 20 | $Na_2WO_4$ | $(HOCH_2)_2P(O)OH$ | $[CH_3(C_8H_{17})_3N]HSO_4$ |
| 21 | $Na_2WO_4$ | $(HOCH_2)_2P(O)OH$ | $[CH_3(C_8H_{17})_3N]HSO_4$ |

The invention also comprises one or more compounds of the formula, $$[R^1{}_nR^2{}_mN+]_3\{PO_4[WO(O_2)_2]_4\},$$

characterized in that $R^1$ and $R^2$ each mean C1-C30 n-alkyl, and $R^1$ is the same as or different from $R^2$, and the sum of m and n is 4.

These compounds can be used as active species of a catalyst in the inventive process and are generated by the mixing of the already named catalyst precursors and phase transfer catalysts in water in the presence of hydrogen peroxide. Examples of these compounds include $[CH_3(C_8H_{17})_3N]_3\{PO_4[WO(O_2)_2]_4\}$, $[(CH_3)_2(C_8H_{17})_2N]_3\{PO_4[WO(O_2)_2]_4\}$, $[CH_3(C_{18}H_{37})_3N]_3\{PO_4[WO(O_2)_2]_4\}$, $[(C_4H_9)_4N]_3\{PO_4[WO(O_2)_2]_4\}$, $[(CH_3)_2(C_{18}H_{37})_2N]_3\{PO_4[WO(O_2)_2]_4\}$, $[(C_{18}H_{37})_4N]_3\{PO_4[WO(O_2)_2]_4\}$, and $[(CH_3)_3(C_{16}H_{33})N]_3\{PO_4[WO(O_2)_2]_4\}$.

The inventive process may also comprise a separation step, such as a separation of the phases, distillation, or/and a chromatographic separation.

The process may be conducted discontinuously or continuously.

The following examples clarify the invention, without limiting it in any way.

General Protocol for Examples 1-15 (Table 1)

$Na_2WO_4$ (0.165 g, 0.50 mmol), $H_3PO_4$, or one of the listed phosphonic acids (0.50 mmol) and a phase transfer catalyst (0.50 mmol) were placed in a 50 mL three-necked flask. 1,9-Cyclohexadecadiene (mixture of isomers, 25 mmol, 5.51 g), $H_2O$ (5.00 g) and toluene (20.00 g) were subsequently added. Two phases were formed: an organic phase consisting of toluene and CHDD, and an aqueous phase containing the precursors for the catalyst. The mixture was then stirred at 800 rpm and heated to the reaction temperature of 60° C. Once this temperature was reached, the first portion of $H_2O_2$ (50 wt %) (0.47 g, 6.91 mmol, 0.27 mol. equiv.) was added and the reaction started. After 60 min, a second portion of $H_2O_2$ was dripped in (0.47 g, 6.91 mmol, 0.27 mol. equiv.). Thereafter, it was stirred for another 2 hours at 60° C. The progress of the reaction was monitored by taking samples from the organic phase every 20 minutes during the first two hours and at the end of the experiment. The determination of conversion, yields, and selectivities was carried out by means of GC/MS.

TABLE 1

| Examples | Phosphorus component | Phase transfer catalyst | t [min] | Conversion of CHDD [%] | Yield of I [%] | Selectivity to I [%] |
|---|---|---|---|---|---|---|
| 1 | $HOCH_2P(O)(OH)_2$ | $[CH_3(C_8H_{17})_3N]Cl$ | 80 | 11.4 | 11.4 | 100 |
| | | | 100 | 16.3 | 15.9 | 97.3 |
| | | | 180 | 30.1 | 27.7 | 92.1 |
| 2 | $HOCH_2P(O)(OH)_2$ | $[CH_3(C_8H_{17})_3N]HSO_4$ | 20 | 11.8 | 11.8 | 100 |
| | | | 40 | 22.1 | 21.1 | 95.6 |
| | | | 60 | 22.7 | 21.7 | 95.2 |
| | | | 80 | 29.2 | 27.2 | 93.2 |
| 3* | $HOCH_2P(O)(OH)_2$ | $[CH_3(C_{18}H_{37})_3N]HSO_4$ | 20 | 12.5 | 12.5 | 100 |
| | | | 40 | 21.6 | 20.1 | 93.3 |
| | | | 60 | 24.2 | 22.4 | 92.5 |

TABLE 1-continued

| Examples | Phosphorus component | Phase transfer catalyst | t [min] | Conversion of CHDD [%] | Yield of I [%] | Selectivity to I [%] |
|---|---|---|---|---|---|---|
| 4 | $C_6H_5P(O)(OH)_2$ | $[CH_3(C_8H_{17})_3N]Cl$ | 100 | 14.8 | 14.8 | 100 |
|  |  |  | 120 | 19.2 | 18.3 | 95.7 |
|  |  |  | 180 | 25.7 | 23.8 | 92.7 |
| 5 | $C_6H_5P(O)(OH)_2$ | $[CH_3(C_8H_{17})_3N]HSO_4$ | 60 | 19.3 | 18.5 | 95.6 |
|  |  |  | 80 | 25.2 | 23.8 | 94.5 |
|  |  |  | 100 | 31.6 | 29.0 | 91.7 |
| 6* | $C_6H_5P(O)(OH)_2$ | $[CH_3(C_{18}H_{37})_3N]HSO_4$ | 60 | 19.4 | 18.3 | 94.3 |
|  |  |  | 80 | 24.3 | 22.7 | 93.7 |
|  |  |  | 100 | 31.3 | 28.8 | 92.1 |
| 7 | $H_2NCH_2P(O)(OH)_2$ | $[CH_3(C_8H_{17})_3N]Cl$ | 60 | 14.8 | 14.5 | 97.9 |
|  |  |  | 80 | 23.3 | 22.4 | 96.2 |
|  |  |  | 100 | 32.5 | 30.2 | 93.0 |
| 8 | $H_2NCH_2P(O)(OH)_2$ | $[CH_3(C_8H_{17})_3N]HSO_4$ | 60 | 13.2 | 13.1 | 99.2 |
|  |  |  | 80 | 23.8 | 22.5 | 94.6 |
|  |  |  | 100 | 34.5 | 31.7 | 91.8 |
| 9 | $H_3PO_4$ | $[(C_4H_9)_4N]HSO_4$ | 120 | 0 | 0 | 0 |
| 10 | $H_3PO_4$ | $[CH_3(C_8H_{17})_3N]Cl$ | 20 | 15.8 | 13.2 | 83.6 |
|  |  |  | 60 | 29.4 | 25.1 | 85.4 |
|  |  |  | 100 | 42.1 | 34.4 | 81.8 |
| 11 | $H_3PO_4$ | $[CH_3(C_8H_{17})_3N]HSO_4$ | 20 | 10.9 | 10.7 | 98.7 |
|  |  |  | 40 | 23.8 | 22.7 | 95.3 |
|  |  |  | 60 | 28.7 | 26.6 | 92.7 |
| 12* | $H_3PO_4$ | $[(CH_3)_2(C_{18}H_{37})_2N]HSO_4$ | 20 | 10.1 | 10.1 | 100 |
|  |  |  | 40 | 20.7 | 19.4 | 93.7 |
|  |  |  | 80 | 37.8 | 34.5 | 91.4 |
| 13* | $H_3PO_4$ | $[(C_{18}H_{37})_4N]HSO_4$ | 60 | 6.7 | 6.5 | 97.2 |
|  |  |  | 80 | 14.4 | 14.0 | 97.4 |
|  |  |  | 100 | 23.9 | 22.6 | 94.5 |
|  |  |  | 120 | 31.1 | 28.4 | 91.2 |
| 14 | $H_3PO_4$ | $[(CH_3)_3(C_{16}H_{33})N]O_3S\text{—}C_6H_4\text{-}4\text{-}CH_3$ | 60 | 12.0 | 12.0 | 100 |
|  |  |  | 120 | 24.1 | 23.0 | 95.4 |
|  |  |  | 180 | 33.7 | 31.1 | 92.1 |
| 15* | $H_3PO_4$ | $[CH_3(C_8H_{17})_3N]H_2PO_4$ | 40 | 18.6 | 18.1 | 97.1 |
|  |  |  | 60 | 23.5 | 22.4 | 95.3 |
|  |  |  | 80 | 31.1 | 28.5 | 91.5 |
|  |  |  | 100 | 37.1 | 33.8 | 90.9 |

*A one-half approach was taken with Example 15 (Table 1), using the following amounts: $Na_2WO_4$ (0.083 g, 0.25 mmol), $H_3PO_4$ (0.25 mmol), PTC (0.25 mmol), 1,9-cyclohexadecadiene (2.75 g, 12.5 mmol), toluene (10.0 g), and $H_2O$ (2.5 g), and 2 portions of 50 wt % $H_2O_2$ (0.24 g, 3.53 mmol, each 0.28 mol. equiv.). The reaction procedure was carried out exactly as described in the general protocol for Examples 1-14.

Protocol for Example 16 (Table 2)

$Na_2WO_4$ (0.083 g, 0.25 mmol), diphenylphosphinic acid (0.054 g, 0.25 mmol), and methyltrioctylammonium hydrogen sulfate (0.25 mmol) were placed in a 25 mL, three-necked flask. 1,9-Cyclohexadecadiene (mixture of isomers, 12.5 mmol, 2.75 g), $H_2O$ (2.50 g), and toluene (10.00 g) were subsequently added. Two phases were formed: an organic phase consisting of toluene and CHDD, and an aqueous phase containing the precursors for the catalyst. The mixture was then stirred at 800 rpm and heated to the reaction temperature of 80° C. Once this temperature was reached, the first portion of $H_2O_2$ (50 wt %) (0.24 g, 3.53 mmol, 0.28 mol. equiv.) was added and the reaction started. After 60 min, a second portion of $H_2O_2$ was dripped in (0.24 g, 3.53 mmol, 0.28 mol. equiv.). Thereafter, it was stirred for another 2 hours at 80° C. The progress of the reaction was monitored by taking samples from the organic phase every 20 minutes during the first two hours and at the end of the experiment. The determination of conversion, yields, and selectivities was carried out by means of GC/MS.

TABLE 2

| Example | Phosphorus component | Phase transfer catalyst | t [min] | Conversion of CHDD [%] | Yield of I [%] | Selectivity to I [%] |
|---|---|---|---|---|---|---|
| 16 | $(C_6H_5)_2P(O)OH$ | $[CH_3(C_8H_{17})_3N]HSO_4$ | 20 | 0.2 | 0.2 | 99.0 |
|  |  |  | 40 | 2.0 | 2.0 | 99.0 |
|  |  |  | 60 | 3.2 | 3.1 | 99.0 |
|  |  |  | 80 | 6.2 | 6.1 | 99.0 |
|  |  |  | 100 | 11.7 | 11.3 | 96.6 |
|  |  |  | 120 | 16.2 | 15.6 | 95.9 |
|  |  |  | 180 | 24.1 | 22.4 | 93.0 |
|  |  |  | 240 | 28.6 | 26.0 | 90.9 |

Protocol for Example 17 (Table 3)

$Na_2WO_4$ (0.165 g, 0.50 mmol), aminomethylphosphonic acid (0.50 mmol) and methyltrioctylammonium hydrogen sulfate (0.233 g, 0.50 mmol) were placed in a 50 mL three-necked flask. 1,9-Cyclohexadecadiene (mixture of isomers, 25 mmol, 5.51 g), $H_2O$ (5.00 mL), and 1,2-dichloroethane (20.00 mL) were subsequently added. Two phases were formed: an organic phase consisting of 1,2-dichloroethane and CHDD, and an aqueous phase containing the precursors for the catalyst. The mixture was then stirred at 700 rpm and heated to the reaction temperature of 60° C. Once this temperature was reached, the first portion of $H_2O_2$ (50 wt %) (1.10 g, 16.2 mmol, 0.65 mol. equiv.) was added and the reaction started. After 30 min and 60 min, a second portion of $H_2O_2$ was dripped in (1.10 g, 16.2 mmol, 0.65 mol. equiv. per portion) in each case. Thereafter, it was stirred for another 1.5 hours at 60° C. The progress of the reaction was monitored by taking samples from the organic phase every 20 minutes during the first 100 minutes and at the end of the experiment. The determination of conversion, yields, and selectivities was carried out by means of GC/MS.

TABLE 3

| Example | Phosphorus component | Phase transfer catalyst | t [min] | Conversion of CHDD [%] | Yield of I [%] | Selectivity to I [%] |
|---|---|---|---|---|---|---|
| 17 | $H_2NCH_2P(O)(OH)_2$ | $[CH_3(C_8H_{17})_3N]HSO_4$ | 20 | 5.3 | 5.3 | 99.0 |
| | | | 40 | 12.4 | 12.4 | 99.0 |
| | | | 60 | 25.1 | 23.5 | 93.5 |
| | | | 80 | 36.6 | 33.4 | 91.3 |
| | | | 100 | 44.9 | 40.0 | 89.0 |

Protocol for Example 18 (Table 4)

$H_2WO_4$ (0.125 g, 0.50 mmol), phosphoric acid (0.50 mmol) and methyltrioctylammonium hydrogen sulfate (0.233 g, 0.50 mmol) were placed in a 50 mL three-necked flask. 1,9-Cyclohexadecadiene (mixture of isomers, 25 mmol, 5.51 g), $H_2O$ (5.00 mL), and toluene (20.00 mL) were subsequently added. Two phases were formed: an organic phase consisting of toluene and CHDD, and an aqueous phase containing the precursors for the catalyst. The mixture was then stirred at 700 rpm and heated to the reaction temperature of 60 CC. Once this temperature was reached, the first portion of $H_2O_2$ (50 wt %) (0.74 g, 10.9 mmol, 0.43 mol. equiv.) was added and the reaction started. After 30 min and 60 min, a second portion of $H_2O_2$ was dripped in (0.74 g, 10.9 mmol, 0.43 mol. equiv. per portion) in each case. Thereafter, it was stirred for another 1.5 hours at 60 CC. The progress of the reaction was monitored by taking samples from the organic phase every 20 minutes during the first 100 minutes and at the end of the experiment. The determination of conversion, yields, and selectivities was carried out by means of GC/MS.

Protocol for Example 19 (Table 5)

$Na_2WO_4$ (0.165 g, 0.50 mmol), hydroxymethylphosphonic acid (0.50 mmol), and methyltrioctylammonium hydrogen sulfate (0.50 mmol) were placed in a 25 mL, three-necked flask. 1,9-cyclohexadecadiene (mixture of isomers, 25 mmol, 5.51 g) and $H_2O$ (5.00 g) were subsequently added. Two phases were formed: an organic phase consisting of CHDD and an aqueous phase containing the precursors for the catalyst. The mixture was then stirred at 800 rpm and heated to the reaction temperature of 60° C. Once this temperature was reached, the first portion of $H_2O_2$ (50 wt %) (0.47 g, 6.91 mmol, 0.27 mol. equiv.) was added and the reaction started. After 60 min, a second portion of $H_2O_2$ was dripped in (0.47 g, 6.91 mmol, 0.27 mol. equiv.). Thereafter, it was stirred for another 2 hours at 60° C. The progress of the reaction was monitored by taking samples from the organic phase every 20 minutes during the first two hours and at the end of the experiment. The determination of conversion, yields, and selectivities was carried out by means of GC/MS.

TABLE 4

| Example | Phosphorus component | Phase transfer catalyst | t [min] | Conversion of CHDD [%] | Yield of I [%] | Selectivity to I [%] |
|---|---|---|---|---|---|---|
| 18 | $H_3PO_4$ | $[CH_3(C_8H_{17})_3N]HSO_4$ | 20 | 24.7 | 24.7 | 99.0 |
| | | | 40 | 44.0 | 41.6 | 94.5 |
| | | | 60 | 57.2 | 50.6 | 88.4 |

TABLE 5

| Example | Phosphorus component | Phase transfer catalyst | t [min] | Conversion of CHDD [%] | Yield of I [%] | Selectivity to I [%] |
|---|---|---|---|---|---|---|
| 19 | $HOCH_2P(O)(OH)_2$ | $[CH_3(C_8H_{17})_3N]HSO_4$ | 40 | 13.6 | 13.6 | 99.0 |
| | | | 100 | 28.5 | 27.0 | 94.9 |
| | | | 120 | 36.5 | 32.6 | 89.4 |

Protocol for Example 20 (Table 6)

$Na_2WO_4$ (0.083 g, 0.25 mmol), bis(hydroxymethyl)phosphinic acid (0.031 g, 0.25 mmol), and methyltrioctylammonium hydrogen sulfate (0.25 mmol) were placed in a 25 mL, three-necked flask. 1,9-Cyclohexadecadiene (mixture of isomers, 12.5 mmol, 2.75 g), $H_2O$ (2.50 g), and toluene (10.00 g) were subsequently added. Two phases were formed: an organic phase consisting of toluene and CHDD, and an aqueous phase containing the precursors for the catalyst. The mixture was then stirred at 800 rpm and heated to the reaction temperature of 60° C. Once this temperature was reached, the first portion of $H_2O_2$ (50 wt %) (0.24 g, 3.53 mmol, 0.28 mol. equiv.) was added and the reaction started. After 60 min, a second portion of $H_2O_2$ was dripped in (0.24 g, 3.53 mmol, 0.28 mol. equiv.). Thereafter, it was stirred for another 2 hours at 60° C. The progress of the reaction was monitored by taking samples from the organic phase every 20 minutes during the first two hours and at the end of the experiment. The determination of conversion, yields, and selectivities was carried out by means of GC/MS.

TABLE 6

| Example | Phosphorus component | Phase transfer catalyst | t [min] | Conversion of CHDD [%] | Yield of I [%] | Selectivity to I [%] |
|---|---|---|---|---|---|---|
| 20 | $(CH_2OH)_2P(O)OH$ | $[CH_3(C_8H_{17})_3N]HSO_4$ | 20 | 2.5 | 2.5 | 99 |
| | | | 40 | 6.3 | 6.3 | 99 |
| | | | 60 | 11.3 | 11.3 | 99 |
| | | | 80 | 20.8 | 20.5 | 98.6 |
| | | | 100 | 29.2 | 28.4 | 97.3 |
| | | | 120 | 32.4 | 30.7 | 94.9 |
| | | | 180 | 45.7 | 40.8 | 89.3 |

Protocol for Example 21 (Table 7)

$Na_2WO_4$ (0.083 g, 0.25 mmol), bis(hydroxymethyl)phosphinic acid (0.031 g, 0.25 mmol), and methyltrioctylammonium hydrogen sulfate (0.25 mmol) were placed in a 25 mL, three-necked flask. 1,9-Cyclohexadecadiene (mixture of isomers, 12.5 mmol, 2.75 g), $H_2O$ (2.50 g), and toluene (10.00 g) were subsequently added. Two phases were formed: an organic phase consisting of toluene and CHDD, and an aqueous phase containing the precursors for the catalyst. The mixture was then stirred at 800 rpm and heated to the reaction temperature of 80° C. Once this temperature was reached, the first portion of $H_2O_2$ (50 wt %) (0.24 g, 3.53 mmol, 0.28 mol. equiv.) was added and the reaction started. After 60 min, a second portion of $H_2O_2$ was dripped in (0.24 g, 3.53 mmol, 0.28 mol. equiv.). Thereafter, it was stirred for another 2 hours at 80° C. The progress of the reaction was monitored by taking samples from the organic phase every 20 minutes during the first two hours and at the end of the experiment. The determination of conversion, yields, and selectivities was carried out by means of GC/MS.

TABLE 7

| Example | Phosphorus component | Phase transfer catalyst | t [min] | Conversion of CHDD [%] | Yield of I [%] | Selectivity to I [%] |
|---|---|---|---|---|---|---|
| 21 | $(CH_2OH)_2P(O)OH$ | $[CH_3(C_8H_{17})_3N]HSO_4$ | 20 | 12.2 | 12.1 | 99.0 |
| | | | 60 | 27.1 | 26.4 | 97.2 |
| | | | 80 | 39.7 | 35.2 | 88.5 |
| | | | 100 | 45.5 | 39.4 | 86.5 |
| | | | 120 | 47.4 | 38.9 | 82.1 |

The invention claimed is:

1. Process for producing 17-oxabicyclo[14.1.0]heptadec-8-ene comprising a reaction with reactants including cyclohexadeca-1,9-diene and hydrogen peroxide.

2. Process according to claim 1, characterized in that the reaction is carried out in a two-phase system.

3. Process according to claim 1, characterized in that the reaction is carried out in the presence of a catalyst.

4. Process according to claim 3, characterized in that the catalyst contains phosphorus.

5. Process according to claim 4, characterized in that the catalyst contains tungsten.

6. Process according to claim 5, characterized in that an active species of the catalyst contains peroxotungstophosphate.

7. Process according to claim 6, characterized in that the active species of the catalyst contains $\{PO_4[WO(O_2)_2]_4\}^{3-}$ as an anion.

8. Process according to claim 7, characterized in that the active species of the catalyst contains a tetraalkylammonium cation.

9. Process according to claim 8, characterized in that the tetraalkylammonium cation has the formula, $R^1{}_nR^2{}_mN^+$, characterized in that $R^1$ and $R^2$ each mean C1-C30 n-alkyl, and
$R^1$ is the same as or different from $R^2$,
and the sum of m and n is 4.

10. Process according to claim 3, characterized in that an active species of the catalyst is formed from at least one phosphorus-containing acid, at least one tungsten (VI)-compound, and at least one phase transfer catalyst.

11. Process according to claim 10, characterized in that:
the phosphorus-containing acid is selected from the group consisting of phosphoric acid, a phosphonic acid, a phosphinic acid, and an heteropoly acid;
the tungsten (VI)-compound is selected from the group consisting of an alkali tungstate, an alkaline-earth tungstate, an ammonium tungstate, and a tungsten trioxide monohydrate; and
the phase transfer catalyst is a tetraalkylammonium salt having the formula, $(R^1{}_nR^2{}_mN^+)_y X^{y-}$, characterized in that $R^1$ and $R^2$ each mean C1-C30 n-alkyl, and $R^1$ is the same as or different from $R^2$, $X^{y-}$ equals $Cl^-$, $BR^-$, $I^-$, $HSO_4^-$, $SO_4^{2-}$, $H_2PO_4^-$, $HPO_4^{2-}$, $PO_4^{3-}$, $CH_3SO_3^-$, $CF_3SO_3^-$, $CH_3C_6H_4SO_3^-$, $ClO_3^-$, $ClO_4^-$, or $NO_3^-$, and the sum of m and n equals 4, and y equals 1, 2, or 3.

12. Process according to claim 1, characterized in that the reaction is carried out in the presence of a compound of the formula $[R^1{}_nR^2{}_mN^+]_3\{PO_4[WO(O_2)_2]_4\}$, characterized in that $R^1$ and $R^2$ each mean C1-C30 n-alkyl, $R^1$ is the same as or different from $R^2$, and the sum of m and n is 4.

* * * * *